(12) United States Patent
Berube-Lauziere et al.

(10) Patent No.: US 7,862,335 B2
(45) Date of Patent: Jan. 4, 2011

(54) SYSTEM AND METHOD FOR DETECTION OF DENTAL TARTAR

(75) Inventors: Yves Berube-Lauziere, Quebec (CA); Naim Karazivan, Laval (CA); Emmanuel Montini, Laval (CA); Sophie Bernier, Quebec (CA); Marc Levesque, St-Augustin (CA); Yvan Mimeault, Cap-Rouge (CA); Michel Doucet, Saint-Augustin-De-Desmaures (CA)

(73) Assignee: Dentsply Canada Ltd., Woodbridge, Ontario (CA)

( * ) Notice: Subject to any disclaimer, the term of this patent is extended or adjusted under 35 U.S.C. 154(b) by 122 days.

(21) Appl. No.: 10/181,904

(22) PCT Filed: Jan. 22, 2001

(86) PCT No.: PCT/CA01/00063

§ 371 (c)(1),
(2), (4) Date: Dec. 26, 2002

(87) PCT Pub. No.: WO01/52723

PCT Pub. Date: Jul. 26, 2001

(65) Prior Publication Data

US 2003/0143510 A1     Jul. 31, 2003

(30) Foreign Application Priority Data

Jan. 21, 2000     (CA) .................................. 2297476

(51) Int. Cl.
*A61C 1/00*     (2006.01)

(52) U.S. Cl. ...................................................... 433/29

(58) Field of Classification Search .................... 433/29, 433/86, 119, 215, 216; 356/317, 318, 341; 600/410, 411, 476, 477; 385/12, 31, 369
See application file for complete search history.

(56) References Cited

U.S. PATENT DOCUMENTS 4,204,328 A   *   5/1980   Kutner ......................... 433/29

(Continued)

FOREIGN PATENT DOCUMENTS

DE             4015066 A1     11/1991

(Continued)

OTHER PUBLICATIONS

Definition of "spectral reflectance" by the Academic Press Dictionar of Science and Technology. 1992,1996.*

(Continued)

*Primary Examiner*—Cris L Rodriguez
*Assistant Examiner*—Sunil K Singh
(74) *Attorney, Agent, or Firm*—Anglehart et al.

(57) ABSTRACT

A dental tartar detection system (10), especially for detection of subgingival tartar (S), comprises a probe (12) adapted to be displaced along a tooth (T), an illumination system (14) for illuminating with an incident light a region on the tooth (T), a detection system (16) for collecting the light reflected thereat, and an analysis system (34) for providing a signal to an operator of the probe (12) when measurements on the reflected light in one or more predetermined range of wavelengths fall within any predetermined range of values that are characteristic of tartar (S). Typically, the detection of tartar (S) is achieved on the basis of the possible colors that tartar (S) can have such that the aforementioned one or more predetermined range of values cover wavelengths associated with colors of tartar (S).

60 Claims, 6 Drawing Sheets

U.S. PATENT DOCUMENTS

| | | | |
|---|---|---|---|
| 4,479,499 A * | 10/1984 | Alfano | 600/477 |
| 4,790,751 A | 12/1988 | Reinhardt et al. | |
| 4,858,001 A | 8/1989 | Millbank et al. | |
| 5,230,621 A | 7/1993 | Jacoby | |
| 5,306,144 A | 4/1994 | Hibst et al. | |
| 5,328,365 A | 7/1994 | Jacoby | |
| 5,382,163 A | 1/1995 | Putnam | |
| 5,501,596 A * | 3/1996 | Bailey | 433/86 |
| 5,527,262 A | 6/1996 | Monroe et al. | |
| 5,562,448 A | 10/1996 | Mushabac | |
| 5,570,182 A * | 10/1996 | Nathel et al. | 356/511 |
| 5,587,284 A | 12/1996 | Brattesani | |
| 5,735,792 A | 4/1998 | Vanden Hoek et al. | |
| 5,880,826 A | 3/1999 | Jung et al. | |
| 5,961,327 A * | 10/1999 | Lohn | 433/80 |
| 6,024,562 A | 2/2000 | Hibst et al. | |
| 6,053,731 A | 4/2000 | Heckenberger | |
| 6,095,810 A * | 8/2000 | Bianchetti | 433/29 |
| 6,102,704 A * | 8/2000 | Eibofner et al. | 433/215 |
| 6,135,774 A * | 10/2000 | Hack et al. | 433/215 |
| 6,179,611 B1 * | 1/2001 | Everett et al. | 433/29 |
| 6,186,780 B1 * | 2/2001 | Hibst et al. | 433/29 |
| 6,561,802 B2 | 5/2003 | Alexander | |
| 2001/0023057 A1 * | 9/2001 | Alexander | 433/29 |

FOREIGN PATENT DOCUMENTS

| | | |
|---|---|---|
| DE | 93 17 984.7 U | 5/1995 |
| DE | 29704185 U1 | 6/1997 |
| DE | 29705934 U1 | 7/1997 |
| EP | 0 326 497 B1 | 11/1993 |
| EP | 0 774 235 A1 | 5/1997 |
| EP | 0 653 051 B2 | 11/2001 |
| EP | 0 914 809 B1 | 2/2003 |
| JP | 08071092 A * | 3/1996 |
| WO | WO 99/01746 | 1/1999 |

OTHER PUBLICATIONS

Run-Zhi Hou et al., Fourier Transform Infrared Photoacoustic Spectroscopy of Dental Calculus; Mikrochimica Acta (Wien); 1988; 11, 133-136.

The Encyclopedia of Sustainable Energy and Alternate Living, Definition of "Spectral Reflectance" http://www.daviddarling.info/encyclopedia/S/AE_spectral_reflectance.html.

PC-Based Digital Lock-In Detection of Small Signals in the Presence of Noise, Philip Kromer, Ralph Robinett, Roger Bengtson, Charles Hays, http://mrflip.com/papers/LIA/AAPTPaper/AAPTPaper.PDF.

* cited by examiner

SYSTEM AND METHOD FOR DETECTION OF DENTAL TARTAR

BACKGROUND OF THE INVENTION

1. Field of the Invention

The present relates to the detection of dental tartar and, more particularly, to the detection of subgingival tartar.

2. Description of the Prior Art

Figure 2:
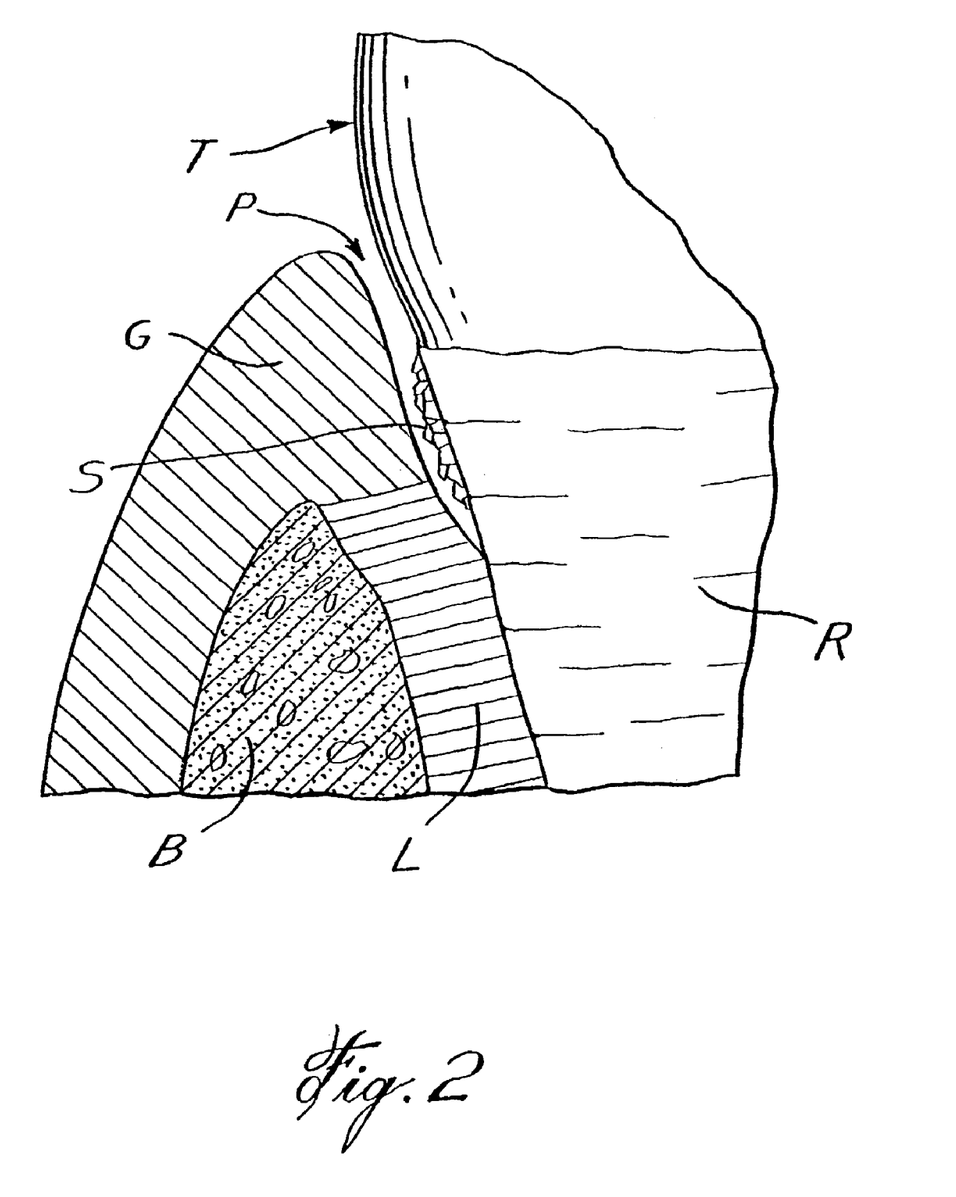
FIG. 2 is a schematic view similar to FIG. 1 but showing a periodontal pocket between the tooth's root and the gums, with subgingival tartar being shown lodged therein.

The removal of tartar, for instance with a scraper or a sonic or ultrasonic instrument, is important to prevent or to treat periodontal diseases, i.e. of tissues which surround the teeth, such as bone B, gums G, ligaments, etc. The tartar is calcified dental plaque that has accumulated on the tooth surface. Supergingival tartar and subgingival tartar S (see FIG. 2) must be removed as tartar is a porous substance which contains bacteria and which favours the accumulation of these pathogenic bacteria on its structure. Moreover, tartar mechanically irritates the gums.

Figure 1:
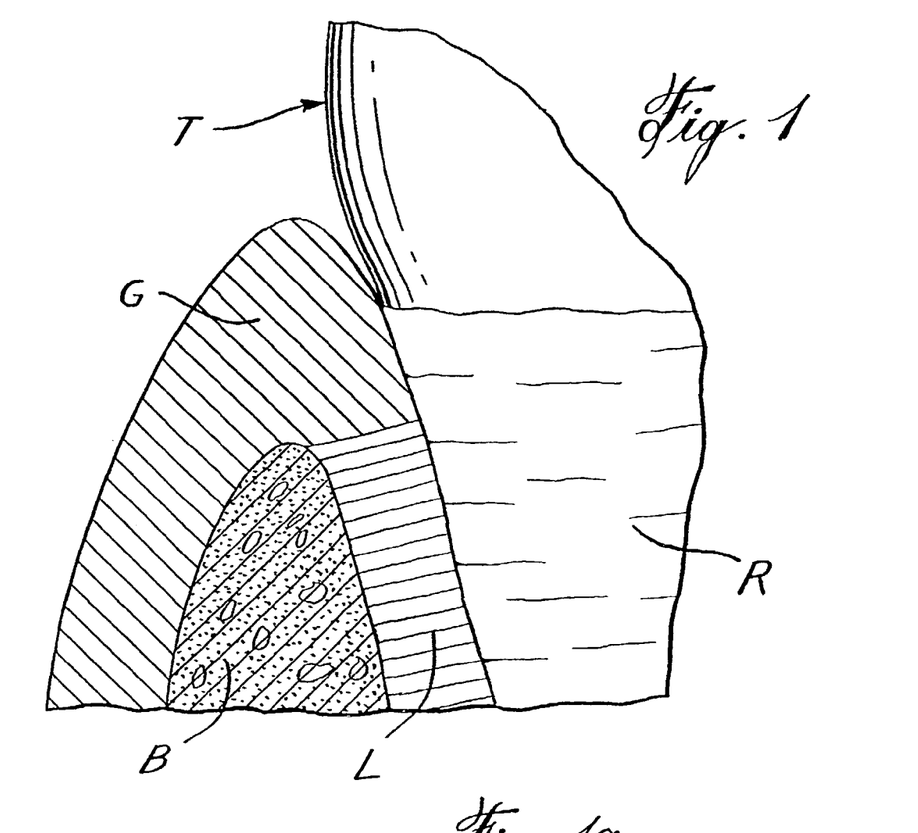
Figure 1A:
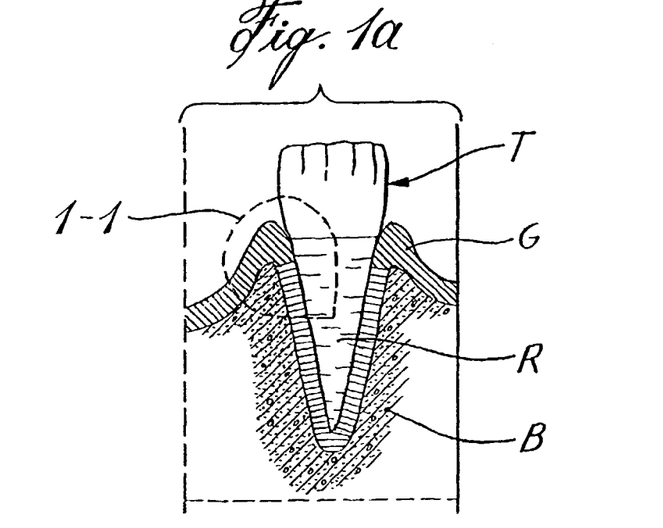
FIG. 1a is a schematic vertical cross-sectional view of a tooth and its surrounding tissues.

In a healthy periodontium (see FIG. 1) there is no periodontal pocket. However, when there is a periodontal disease (FIG. 2), such a periodontal pocket P is formed by an inner surface of the gums G and by the root R of the tooth T and which is closed apically by the periodontal ligaments L. Subgingival tartar S can thus be found in this periodontal pocket P.

Therefore, to prevent periodontal problems which can lead to severe health problems, it is important to remove tartar from the tooth surface as it is forming; on the other hand, the removal of tartar is done with difficulty and in a groping manner, subgingival tartar being normally invisible to the human eye in normal conditions as it is covered by the gums. To remove subgingival tartar (i.e. located behind the gum), the operator must try to locate tartar by tactile feeling using a probe, but one cannot actually view subgingival tartar to ensure a complete removal thereof without resorting to invasive surgical procedures.

The use of an endoscopic method and device for the removal of subgingival tartar is also known from U.S. Pat. Nos. 5,230,621 and No. 5,328,365. In this system, an endoscopic probe is inserted in the gingival pocket or sulcus to endoscopically visualise the process of and/or effects of subgingival root planing, scaling or other plaque removal procedures carried out by other operative instruments. Alternatively, the endoscopic viewing apparatus may be incorporated in an operative instrument which itself is used to remove deposited material from subgingival tooth surfaces, whereby the operator may view and/or guide the instrument while using the plaque removal instrument itself. Therefore, the operator looks at a monitor that provides images of the endoscopic viewing and the operator detects the presence of subgingival tartar by looking at the monitor. This system is efficient, but somewhat cumbersome to use as the operator must stop looking into the mouth of the patient in order to look at the monitor. Moreover, this system is relatively expensive, as it requires a monitor and associated hardware.

Therefore, there is a need for a dental instrument which, using a probe or the like, can automatically detect the presence of subgingival tartar, which does not require the use of a monitor, and which allows the operator to concentrate on his/her task in the patient's mouth by not having to look at a monitor and thus leave the patient's mouth from his/her sight. Such an instrument would facilitate the operator's task of removing subgingival tartar by providing a system which assists the operator in the diagnostic.

SUMMARY OF THE INVENTION

It is therefore an aim of the present invention to provide a novel system for the detection of dental tartar, including subgingival tartar.

It is also an aim of the present invention to provide a novel system for the detection of dental subgingival tartar that automatically detects the tartar based on its spectral reflectance characteristics (of which colour is a special case).

It is a further aim of the present invention to provide a system in which a visual, sound-based, or other, signal is given following detection of subgingival tartar, wherein this detection results from measurements made in the subgingival region and taken in one or more predetermined ranges of wavelengths that are appropriate for discriminating the spectral reflectance characteristics that constitute a signature of tartar presence.

Therefore, in accordance with the present invention, there is provided a dental tartar detection system, comprising a probe adapted to be displaced along a tooth, illumination means for illuminating with an incident light a region on the tooth, detection means for collecting the light reflected thereat, and an analysing system for providing a signal to an operator of said probe when measurements on the reflected light in one or more predetermined ranges of wavelengths fall within any first predetermined range of values that are characteristic of tartar, or when said measurements do not fall within any second predetermined range of values that are characteristic of artefacts other than tartar.

Also in accordance with the present invention, there is provided a method for removing dental tartar from teeth, comprising the steps of: (a) providing an incident light on a region of a tooth, (b) collecting and measuring reflected light from said region of the tooth; (c) analysing said reflected light to determine if said reflected light is representative of the presence of tartar; and (d) providing a signal to an operator of a tartar removal apparatus when presence of tartar has been detected in step (c).

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is an enlarged view of bubble 1-1 of FIG. 1a;

DESCRIPTION OF THE PREFERRED EMBODIMENTS

The present invention is a system 10 for the automated detection of the presence of subgingival tartar S with an endoscopic-like exploration device using an optical method based on the spectral reflectance properties of tartar to discriminate the tartar present on the teeth from the healthy areas thereof, from the gums, from blood, and in fact from any artefact other than tartar that a probe may encounter when it is inserted between a tooth and the gums.

More particularly, the system 10 comprises three main mechanisms, that is (1) a buccal probe, (2) a casing containing optical components, light sources, and acquisition and signal processing electronics, as well as a water inlet capable of being connected to a water supply, and (3) a cable strand that includes optical fibres and a water supply tube and which connects the probe to the casing.

Figure 3:
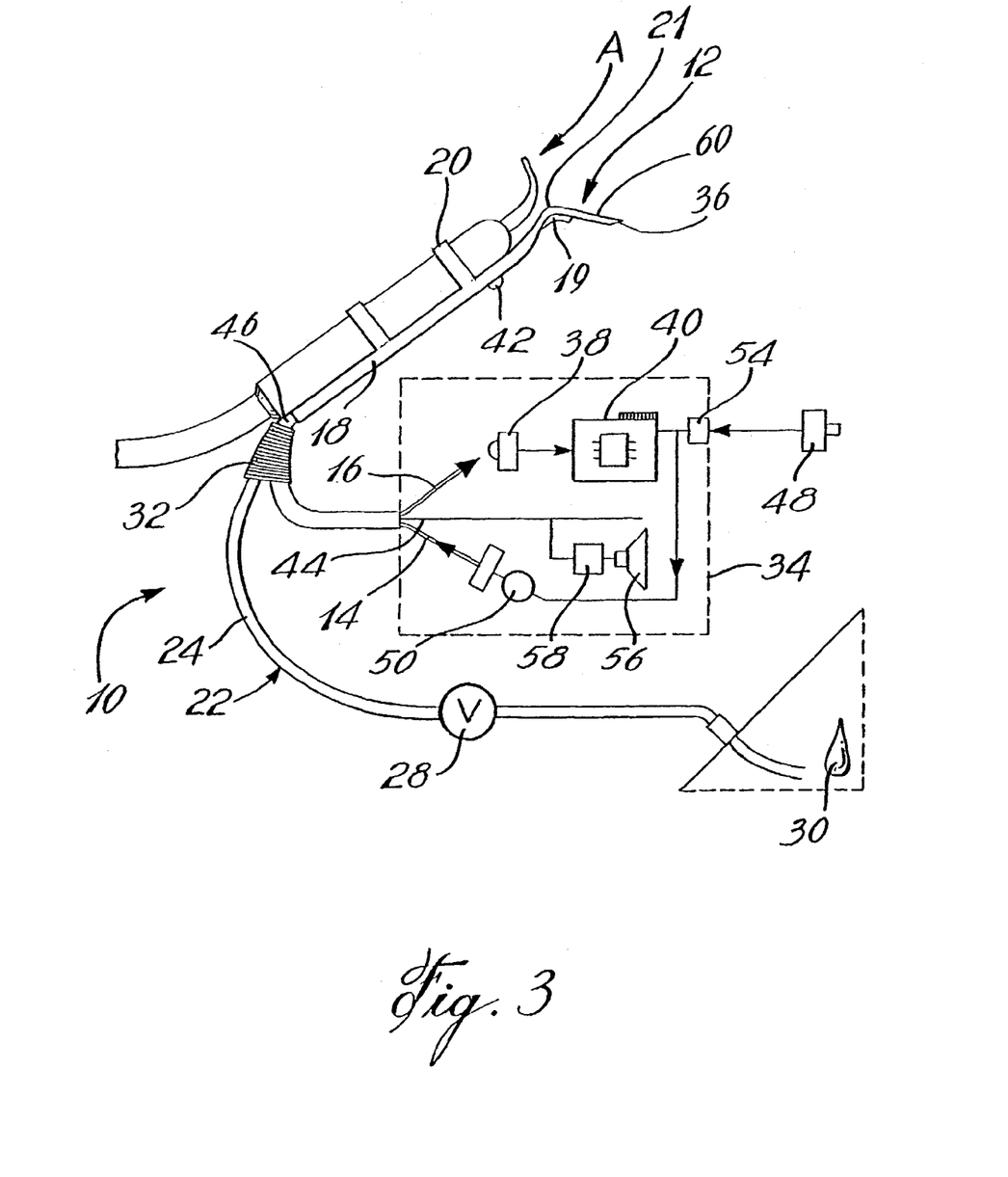
FIG. 3 is a schematic representation of a system for the detection of dental tartar in accordance with the present invention.

Indeed, the system 10 comprises a periodontal probe 12, containing optical fibres and, more particularly, one or more illumination fibres 14 used for illuminating the subgingival region and one or more detection fibres 16 for receiving the light reflected by the tooth T for the subsequent determination of the spectral reflectance characteristics in this region. It is contemplated that a single optical fibre could be used for both illumination and detection functions. The probe 12 has a curved pointy end section 60 with the illumination fibres 14 and detection fibres 16 being contained in the pointy end section 60 and extending up to an open free or distal end 36 thereof and having their respective distal ends thereat.

The probe 12 includes a handle 18 and may include an attachment mechanism 20 so that it may be installed on various apparatuses A used for removing dental tartar S by way of ultrasounds or any other suitable removal technique. It is possible to incorporate the spectral reflectance detection technique described herein which uses fibre optics technology in such tartar removing instruments A to further integrate together the diagnostic and the treatment in a single instrument. The probe 12 also includes a connector on the proximal end of the handle 18 and an irrigation micro-system 22 to clean the site, that is the subgingival region, by injecting water in the periodontal pocket P, in order to provide for further detection efficiency.

The irrigation micro-system 22 includes communicating first and second water supply tubes 24 and 26, respectively, a valve 28 on the first water supply tube 24 and water source 30. The second water supply tube 26 extends through the handle 18 with a distal section thereof 19 (made of stainless steel or other biocompatible material, e.g. plastic or other) extending outwardly of the handle 18. The distal section 19 of the second water supply tube 26 extends out of the handle 18 along the curved pointy end section 60 and terminates short or upstream of the distal end 36 of the curved pointy end section 60 and thus also of the distal ends of the illumination and detection fibres 14 and 16 such as to project water to the distal end 36 of the probe 12 so that blood or any other debris can be evacuated therefrom.

A cable strand 32 links the probe 12 to an electronic system that is provided in a casing 34 which could have the shape and size of a portable cassette player (i.e. a Walkman™) which would be adapted to be connected to an outside power supply (unless the casing 34 may be powered with batteries placed in it) and to the water source 30, thereby rendering the system 10 portable. The light propagated by distal sections of the illumination and detection fibres 14 and 16 in the probe 12 is thus further conveyed to or from the casing 34 by proximal sections of these fibres 14 and 16 that are part of the cable strand 32. The cable strand 32 carries and protects the illumination and detection fibres 14 and 16 and the first water supply tube 24. The cable strand 32 is detachably connected to the connector provided at a proximal end 33 of the handle 18 of the probe 12 so that the probe 12 can be detached from the cable strand 32 for allowing the probe 12 to be sent alone to an autoclave for its sterilisation. The probe 12 could also be of the single-use type and would thus be discarded instead of sterilised.

Each of the one or more illumination fibres 14 provided to illuminate the site (i.e. the periodontal pocket P) has one of its extremities facing a light source (which may be provided or not with an optical wavelength selective filter) and its other extremity at the distal free end 36 of the probe 12. Each such fibre 14 is interrupted (or sectioned) at the connector between the cable strand 32 and the probe 12.

Each of the one or more detection fibres 16 (which may be the same one as that or those optical fibres 14 used for illuminating the periodontal pocket P) is used for receiving the reflected light coming from the periodontal site. Each such detection fibre 16 has one of its extremities at the distal end 36 of the probe 12 and its other extremity facing a photodetector (or an electronic light transducer) 38 (which may or may not comprise an optical wavelength selective filter). Each such fibre 16 is interrupted (or sectioned) at the connector between the cable strand 32 and the probe 12.

This detector 38 is connected to an electronic system housed in the casing 34.

At the detector or from the signal delivered by the detector, there may be an electronic or physical (optical) filtration system to remove from the received wavelengths those that result from non-tartar structures. The signal obtained after this filtering is then analysed by an electronic processor to determine whether tartar is present at the distal end 36 of the probe 12 or not.

If tartar is detected, an indicator (luminous, sound, or any other means sensible by the operator) is actuated so that the operator is informed of the presence of tartar in the region being examined by the distal end of the probe 12. For instance, the indicator can take the form of a luminous indicator 42 located on the probe 12 to which light generated in the casing 34 is conveyed by one or more optical fibres 44 between the casing 34 and the handle 18 of the probe 12 such as to terminate at the indicator 42 provided on the handle 18, and such that the operator can see the light conveyed by the optical fibres 44 upon detection of tartar. Also, the luminous signal could come from a warning LED (light emitting diode) positioned on the handle 18 and electrically connected to a switch located in the casing 34 and triggered automatically upon detection of tartar.

Figures 4, 4A:
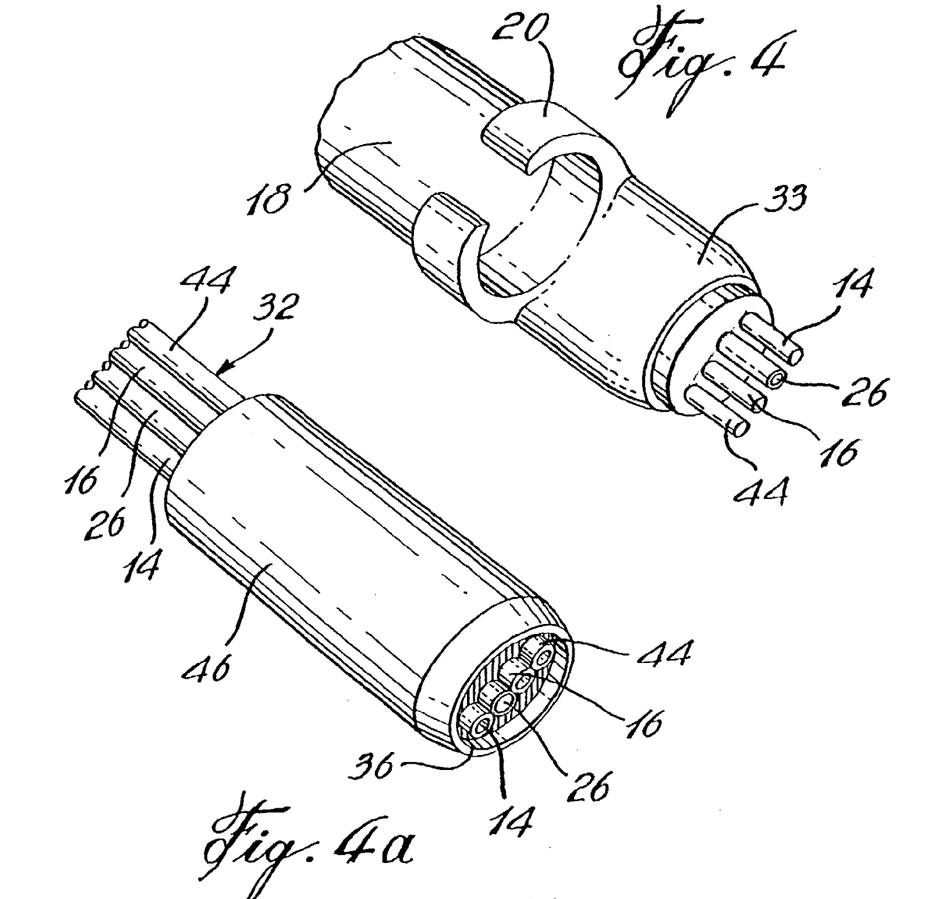
FIGS. 4 and 4a are schematic enlarged partial detailed views of the detection system of FIG. 3.

A connector 46 at the end of the cable strand 32 provides a detachable connection mechanism between the handle 18 of the probe 12 and the cable strand 32 (see FIGS. 4 and 4a). The cable strand 32 is again a flexible sheath for the illumination and detection optical fibre(s) 14 and 16, the first water supply tube 24 and the optical fibre(s) 44 for the luminous indicator 42 on the probe 12, if any.

The casing 34 includes an electrical input power supply 48 (the power supply can be internal or external), one or more light sources 50 (halogen bulb, laser or diode) which may be or not filtered by an optical wavelength selective filter, the photodetector 38, an electronic processor and memory chip with an input for an electronic card 40 (which could serve for example to store information), or the like, an interrupter or switch 54, and a speaker 56 with an amplifier 58 to emit sounds to warn the operator of the presence of tartar.

The valve 28 is provided on the first water supply tube 24, the latter being flexible and being connected at one end thereof to the handle 18 of the probe 12 and at another end thereof to the water source 30. The valve 28 allows for the flow of water to be adjusted.

Therefore, the system 10 can transmit light having an appropriate spectral composition via the illumination fibre(s) 14 onto the tooth's surface and can retrieve the light reflected by the tooth's surface via the detection fibre(s) 16 which may, or not, be distinct from the illumination fibre(s) 14. This reflected light is then detected by a photodetector present in the casing 34 such as to be analysed. Depending on how the spectral composition of the incident light is altered by the reflection thereof on the tooth's surface, an algorithm allows to determine from the photodetector signal if the probe 12 is viewing, or not, tartar. Therefore, if the spectral composition of the reflected light falls within the range or ranges previously determined for dental tartar, the algorithm sends a sensory signal to the operator, such as by actuating the luminous indicator 42 on the handle 18 via the optical fibre 44 which conveys light generated in the casing 34 to the indicator 42, although the signal could also be given in the form of sound, vibration, etc.

Figure 4B:
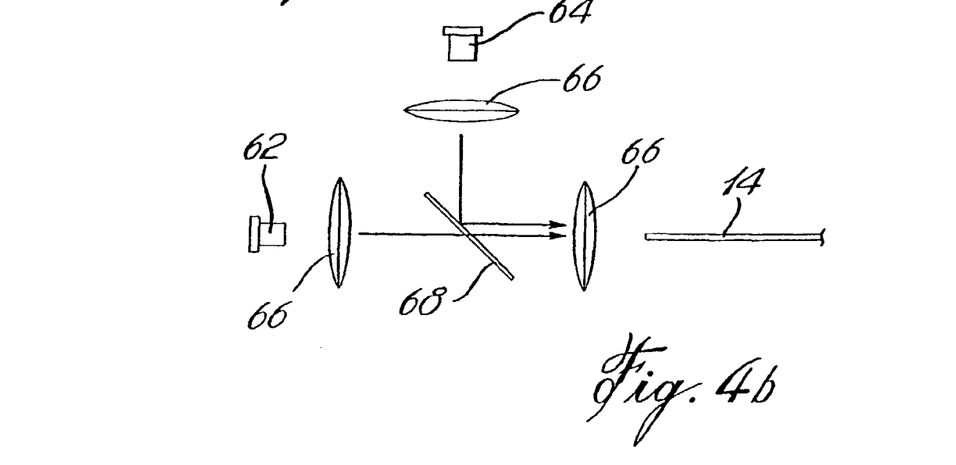
FIG. 4b is a schematic detailed view of some components of the casing of FIG. 3.

With reference particularly to FIG. 4b, the illumination fibre(s) 14 is (are) used to carry light from two LEDs 62 and 64, having different emission spectra and located in the casing 34, up to the distal end 36 of the probe 12. The light emitted by the two LEDs 62 and 64 is coupled into the illumination fibre(s) 14 and, for this coupling, a dichroic mirror is used, also called a dichroic beamsplitter, as it is selective in wavelengths in transmitting light to pass within a range of wavelengths while reflecting light in another range of wavelengths. Such a dichroic mirror or dichroic beamsplitter is also called hot mirror or cold mirror, depending on the wavelength ranges for which the mirror is reflective or transmissive. A set of lenses in a "Y" configuration, or any suitable means, may also be used instead of the dichroic mirror or dichroic beamsplitter to combine the light beams emitted by the LEDs 62 and 64 and couple them into the illumination fibre(s) 14. In FIG. 4b, which illustrates the coupling in the illumination fibre 14, numeral 66 refers to lenses while numeral 68 is for the dichroic beamsplitter which is at 45° and which transmits the light in the wavelength range emitted by LED 62 and reflects the light in the wavelength range emitted by LED 64.

The LEDs 62 and 64 are chosen based on the spectral bands in which the reflectance properties of tartar are different from the reflectance properties of the other artefacts which could possibly be encountered by a probe inserted between a tooth and its gum (healthy parts of the tooth and gum), and this even when blood is present. In fact, in these spectral bands, the spectral transmission of blood has minimal effect. The choice of the spectral bands was determined by a spectral study of the reflectance properties of tartar for the wavelength range of the electromagnetic spectrum between 400 nm and 1,000 nm. This spectral study was conducted in the presence and in the absence of blood. LED 62 emits in the red area of the spectrum and its emission spectrum has its peak at approximately 625 nm and extends from 600 nm to 650 nm. For LED 64, its emission spectrum extends between 800 nm and 920 nm. The LEDs 62 and 64, or any other appropriate light source, could also operate with other wavelengths that are appropriate for the discrimination of tartar, such as in the green region of the spectrum.

With respect to the detection principle used in the present system 10, it operates on the basis of the following. The light reflected by the tooth T is received by the detection fibre 16 and is conveyed to a photodiode located in the casing 34 so as to be transduced into an electric signal. The electronic detection of the light reflected by the tooth and transmitted by the detection fibre(s) 16 operates under the "lock-in" detection principle (also referred to as phase-sensitive detection) although other signal processing approaches could be contemplated. Generally, this principle consists in modulating the intensity of a light source at a given and known modulation frequency (which should not be confused with the optical frequency of the light source). The modulated light is sent onto the medium being inspected and the light, resulting from the interaction with the medium, is detected with a photodetector that converts it into an electric signal. This electric signal is then demodulated such as to extract therefrom only its component having the frequency at which the light source was modulated. This principle allows for the detection of very small signals with great efficiency.

In the system 10, there are two light sources (i.e. the LEDs 62 and 64, although there could be more or less, e.g. 3 LEDs) that are modulated at different frequencies, thereby permitting the detection of the light emitted by both LEDs with a single photodiode by demodulating the electric signal of the photodiode at the two modulation frequencies of the LEDs to obtain a measurement of the amount of the light reflected by the tooth in the two spectral bands associated with the LEDs 62 and 64. These levels appear as signals V1 and V2 at the outputs of the two lock-in circuits associated with the emission channels of the LEDs 62 and 64, respectively, and are used by the processing algorithm. The lock-in detection is herein used for two purposes: (1) it allows to electronically separate (at the detection) the light of both chosen spectral bands impinging on a single detector, and (2) the light levels reflected by the tooth and then detected are very weak and the lock-in method is exploited for its sensitivity.

The signals V1 and V2 at the exits of the lock-in circuits are processed in real time by an electronic processor integrated with the rest of the electronic components of the casing 34. The processing algorithm is programmed in this processor. The processing algorithm produces the ratio of these two signals V1 and V2, $y=V1/V2$ (the order in which this ratio is taken is irrelevant). If this ratio is in a range of values associated with tartar (this range having been previously established using calibration measurements), then the probe 12 is located on tartar. In this case, the algorithm sends a signal to activate a warning sound (that can be deactivated by the operator, if desired) and to activate the warning LED in the casing 34 with the light of the warning LED being transmitted through the optical fibre(s) 44 and being visible through the indicator 42 located on the probe handle 18.

To determine the range of values of the ratio y associated with tartar, a large number of measurements are taken on teeth at various healthy locations thereof and where there is tartar, and this with different levels of blood. By knowing, for each of these measurements, if it was taken on a healthy part or where there is tartar, data are obtained for each of these two situations. By bringing the histograms of these data on a graphic, the range of values associated with tartar is determined.

Figure 5:
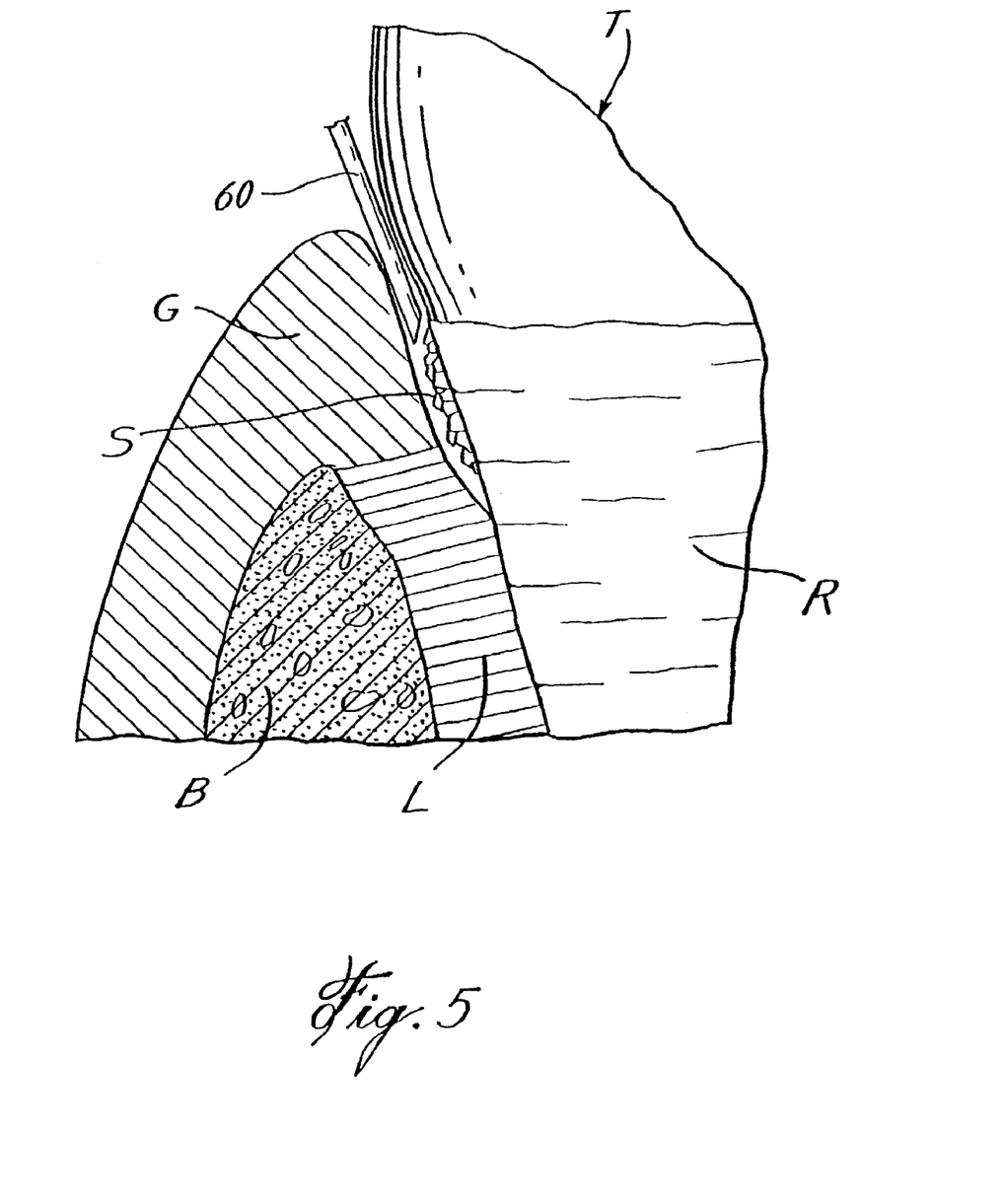
FIG. 5 is a view similar to FIG. 2 but showing the detection of subgingival tartar in the periodontal pocket using the system of the present invention.

In use, the operator mounts the probe 12 of the system 10 of the present invention on the tartar removing apparatus A (although both the detection system 10 and the removal apparatus A could be kept separate from each other during their use). The operator (1) uses the probe 12 to determine where there is tartar and then (2) proceeds to removing the tartar in a conventional manner in regions where tartar has been so detected. The operator then (3) verifies with the probe 12 that the removal of subgingival tartar is complete, and steps (2) and (3) are then repeated until no tartar is detected. To locate tartar with the present detection system 10 in both the above steps (1) and (3), the operator inserts the end section 60 of the probe 12 behind the gum G (i.e. in the periodontal pocket P). The operator then slides the free distal end 36 of the end section 60 of the probe 12 against the surface of the root R of the tooth E, sweeping this surface. The operator must also ensure adequate supply of water to the root R of the tooth E by adjusting the position of the valve 28, which may be manually operated via a foot pedal or a control provided on the handle 18 of the probe 12. When the operator receives a sensory stimulation or signal (e.g. from the illumination of the optical fibre 44, through the indicator 42, or any other means of indication in replacement or in addition to the indicator 42, such as a buzzer, vibrations, etc.) from the electronic system, the operator knows that there is some subgingival tartar at the location of the distal end 36 of the probe 12 and thus visually notes the position of the distal end 36 of the probe 12 such that the operator can then proceed with step (2) which again consists in using the tartar removing apparatus A, for removing the remaining tartar at that location.

Here, for coupling the light from the LEDs 62 and 64, a particular approach has been presented using a dichroic mirror and lenses, but any other configuration, such as a "Y" configuration, which allows to couple the light from the LEDs into the fibres would do as well, the fundamental point being the coupling of light into the fibres.

Figure 6A:
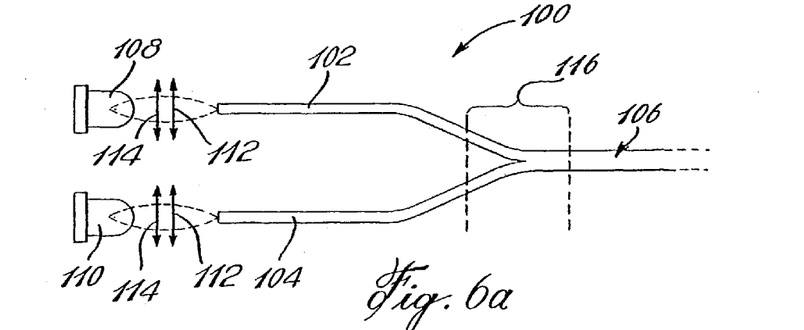
FIGS. 6a, 6b and 6c are schematic views of three methods for combining a number of light beams and coupling them into one or more optical fibres.

For instance, FIG. 6a illustrates a coupling 100 by fusion of two optical fibres 102 and 104 into a single fibre 106. Two LEDs 108 and 110 are used, each emitting light through a pair of lenses 112 and 114. Reference numeral 116 denotes a fused region. This method is commercially known as a WDM coupler.

Figure 6B:
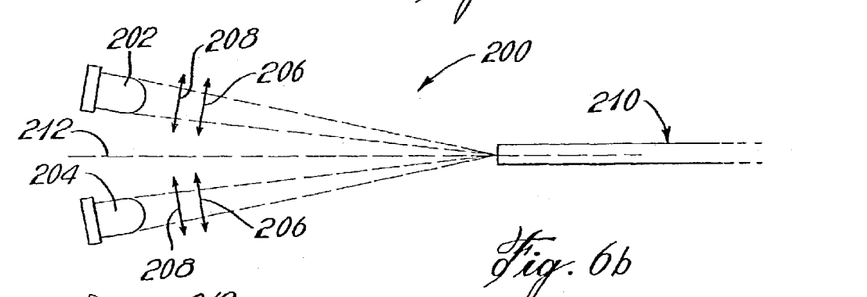

FIG. 6b illustrates another coupling 200 which uses a "Y" configuration to couple the two lights. More particularly, two LEDs 202 and 204 are positioned each behind a pair of lenses 206 and 208 such as to emit light therethrough. The lenses 206 and 208 focalise the light on the extremity of an optical fibre 210. Reference numeral 212 denotes the optical axis of the fibre 210.

Figure 6C:
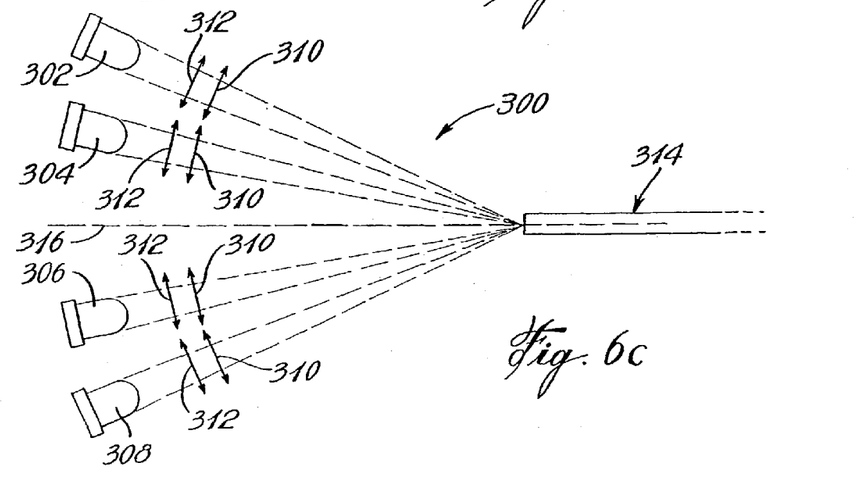

FIG. 6c illustrates a further coupling 300 which also uses a "Y" configuration but here to couple four lights that are produced by four LEDs 302, 304, 306 and 308 positioned each behind a pair of lenses 310 and 312 such as to emit light therethrough. The lenses 310 and 312 focalise the light on the extremity of an optical fibre 314. Reference numeral 316 denotes the optical axis of the fibre 314. It is noted that in a further coupling, also in a "Y" configuration, there could be three LEDs instead of the two and four LEDs found respectively in just-described couplings 200 and 300 of FIGS. 6b and 6c.

Also, as regards the detection principle described above (i.e. the lock-in detection), other principles could be used as well. Any approach that can deliver signals that are sufficiently insensitive to noise to provide for discrimination between tartar and other artefacts that can be found in a periodontal pocket P can be considered. Furthermore, in a numeric system, there could be used for instance two LEDs having different wavelengths (but possibly of same frequency), e.g. a red and a green LED, which are activated repeatedly one after the other and with a delay therebetween.

As an alternative to the processing algorithm presented hereinabove, combinations of the signals V1 and V2 other than the above ratio y could be considered. Indeed, the classification of the data into "is tartar" and "is not tartar" could be done in a two-dimensional space, for instance by plotting V1 versus V2, or any other function of V1 and V2 versus another function of V1 and V2 that is independent from the previous function. Also, if more than two LEDs or other sources of light (such as lasers, halogen lamps, spectral lamps, filtered lamps, etc.) are used, information can be gathered and analysed in two or more dimensions.

Furthermore as an alternative to the approach just described, a spectrometer could be used to measure a spectrum of the light reflected by the tooth and this spectrum would then be analysed with an algorithm to determine if it corresponds to a spectrum of tartar or to a spectrum of another artefact. Any other suitable method may be used to analyse the spectrum received and compare it with the spectrum of tartar with a view to detecting the presence of tartar.

The present system could, by varying the spectrum to be detected, be used to locate other structures having distinctive spectral characteristics and positioned in a buccal site where access is limited (e.g. dental decay).

The system 10 could also include a recalibration function. A warning signal can also be provided to indicate when too much blood is present in the area being examined by the probe 12 and that the system 10 cannot make an adequate reading and thus cannot determine with sufficient precision if tartar is present on the tooth in this area.

A further feature could be included to indicate if the probe 12 or, more specifically, the illumination and/or detection fibres 14 and 16 thereof are too worn out to be efficiently used and should thus be replaced. Such a state could be detected by insufficient light being received in the electronic system provided in the casing 34.

In addition to providing to the operator the luminous (or other) signal that indicates the presence of tartar with an indicator (such as the illustrated optical fibre 44), the system 10 may also include a monitor that displays further information to the operator such as electronic signals within the system which would help his/her diagnostic.

There may also be included a means of collecting data from the electronic system (e.g. via a computer and software, including an electronic card 40, etc.), to be saved in any kind of storing medium for allowing the patient's history to be followed.

For the present embodiment of the system 10, the reflectance properties of tartar in the range between 400 nm and 1,000 nm have been studied, and light sources in that range are used (the two LEDs 62 and 64). However, use of light sources emitting below 400 nm in the ultraviolet (UV) range or above 1,000 nm in the far infrared could also be envisaged.

Also, as the spectral responses of various artefacts other than tartar are known, such as those of enamel, of the tooth's root surface, of the gum, of blood, of tooth decay (caries), of tooth fillings, etc., it is possible to adapt, e.g. program, the system 10 so that a tartar-presence signal is given to the operator as a result of the detection of spectral characteristics that are not representative of those of the aforementioned artefacts. Therefore, if the system 10 detects only spectral characteristics of these artefacts (wherein the term "artefacts" herein excludes tartar), there is no tartar in the region under examination.

As tartar does not respond to UV light, whereas other artefacts do, if UV light is directed onto the tooth, absence of fluorescence may be an indication of the presence of tartar.

Also, a tracing substance could be used, which would adhere to tartar but not to other artefacts. By then illuminating the tooth with a light source, the tracing substance would emit at a specific wavelength such that if this wavelength is detected, tartar is present. It is also possible to use a substance which reacts with the components of tartar such that a spontaneous emission of light at a specific wavelength is emitted. This spontaneous emission of light is collected with the optical probe. If the specific wavelength is detected, there is tartar. This method may possibly be used without a light source at the patient's mouth.

It is also possible for the tartar to be detected using non-luminous wavelengths or by other similar methods, e.g. far infrared, ultraviolet, piezoelectric, ultrasound, magnetic resonance, shadows, etc.

Means other than optical fibres may be used to illuminate the teeth and to collect light reflected therefrom as long as the reflected light is of sufficient intensity to allow it to be analysed.

The illumination fibres 14 and detection fibres 16 and second water supply tube 26 could, instead of being part (downstream of the connector which connects the cable strand 32 to the handle 18) of the probe 12, be incorporated within a tartar removing instrument (using ultrasounds or other means) to further integrate together the tartar detection and removal processes. In such a case, the combined detection and removal instrument would include a switch for alternating between the tartar detection and tartar removing modes. Such a switch could be actuated by the operator or be actuated automatically for switching between the above two modes at an adjustable frequency, e.g. every $1/15$ to $1/100$ second. The combined detection and removal instrument could thus be displaced along the tooth while removing the tartar therefrom and indicating, for instance with a luminous or sound-based indicator, the presence of remaining tartar. This would continue until the indicator of the detection system of the instrument is not actuated.

The invention claimed is:

1. A detection system for detecting and removing dental tartar, comprising:
    a probe configured so as to be displaced along a subgingival portion of a tooth;
    a light source that emits light at one or more wavelengths including at least one wavelength in the infrared range which (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof,
    said probe having a distal end configured to (i) deliver the light from said light source onto the surface of the tooth in the subgingival portion thereof and (ii) receive light reflected from the dental tartar which is disposed on the surface of the tooth in the subgingival portion thereof and beneath said at least one of water or blood during said reflection;
    a spectral reflectance light intensity detector and analyzer configured to (i) receive said reflected light from said probe, (ii) utilize spectral reflectance detection to detect and analyze the at least one wavelength in the infrared range of the light that is reflected from said dental tartar, and (iii) provide a detection signal to an operator of said probe when analysis of the reflected light falls within a first predetermined range of values that are characteristic of dental tartar reflectance properties; and
    ultrasonic tartar removal structure coupled to said probe and configured to remove dental tartar in the subgingival portion of the tooth that is detected by said spectral reflectance light intensity detector and analyzer.

2. A dental tartar detection and removal system as defined in claim 1, wherein said light source comprises a 600 to 650 nm light source and a 800 to 920 nm light source corresponding to the spectral reflectance characteristics of tartar.

3. A dental tartar detection and removal system as defined in claim 1, further comprising at least one optical fibre having a distal end located adjacent said distal end of said probe, and wherein said light source is disposed at a proximal end of said optical fibre such that said incident light emitted by said light source is transmitted by said optical fibre to said distal end thereof and to the tooth.

4. A dental tartar detection and removal system as defined in claim 3, wherein said first predetermined range of values covers wavelengths associated with colours of tartar.

5. A dental tartar detection and removal system as defined in claim 3, further comprising another optical fibre for collecting the reflected light, the distal end of each said optical fibre being located adjacent said distal end of said probe.

6. A dental tartar detection and removal system as defined in claim 3, further comprising an irrigation system for delivering a fluid to a vicinity of the tooth.

7. A dental tartar detection and removal system as defined in claim 6, wherein said irrigation system comprises a fluid supply tube having a distal end thereof adjacent said distal end of each said optical fibre, and a fluid source in fluid communication with said supply tube upstream of the tube distal end.

8. A dental tartar detection and removal system as defined in claim 7, wherein the distal ends of said optical fibre and said supply tube are part of said probe.

9. A dental tartar detection and removal system as defined in claim 8, wherein said optical fibre and said supply tube each comprises a proximal section that is detachably connected to a corresponding said distal section such that said distal sections and said probe are detachable from said proximal sections.

10. A dental tartar detection and removal system as defined in claim 7, wherein said irrigation system comprises a valve for controlling a flow of said fluid.

11. A dental tartar detection and removal system as defined in claim 10, wherein said probe comprises a handle, said handle being provided with a control for operating said valve.

12. A dental tartar detection and removal system as defined in claim 1, wherein said first predetermined range of values covers wavelengths associated with colours of tartar.

13. A dental tartar detection and removal system as defined in claim 1, further comprising an irrigation system for delivering a fluid to a vicinity of the tooth.

14. A dental tartar detection and removal system as defined in claim 1, wherein said light source and said light detector and analyzer each comprises respective proximal and distal sections that are detachably connected together such that said distal sections and said probe are detachable from said proximal sections.

15. A dental tartar detection and removal system as defined in claim 1, wherein said probe further comprises an attachment configured to be detachably mounting said probe to said tartar removal structure such that said detector and analyzer can be used jointly with the removal structure.

16. A dental tartar detection and removal system as defined in claim 15, further comprising a manual switch configured for switching between a removal mode and a detection mode.

17. A dental tartar detection and removal system as defined in claim 15, further comprising a manual switch configured for automatically switching between a removal mode and a detection mode at an adjustable frequency.

18. A dental tartar detection and removal system as defined in claim 1, wherein said probe further comprises at least one optical fibre having a distal end located adjacent a distal end of said probe, said system also comprising a light source disposed at a proximal end of said optical fibre such that said incident light emitted by said light source is transmitted by said optical fibre to said distal end thereof and to the tooth, said system further comprising an irrigation system for delivering a fluid to a vicinity of the tooth, and wherein said probe integrates distal sections of said optical fibre, of said irrigation system and of said removal structure.

19. A dental tartar detection and removal system as defined in claim 1, wherein said removal structure comprises an ultrasound emitting system.

20. A dental tartar detection and removal system as defined in claim 1, wherein said probe comprises a handle.

21. A dental tartar detection and removal system as defined in claim 1, further comprising an indicator actuated by said analyzer to indicate the presence of said dental tartar, said indicator being disposed substantially adjacent a distal portion of said probe.

22. A dental tartar detection and removal system as defined in claim 21, wherein said indicator comprises at least one of a luminous indicator, a sound indicator, and a vibratory indicator.

23. A dental tartar detection and removal system as defined in claim 21, wherein said indicator also comprises a monitor including structure which displays further information to the operator, said information including electronic signals which may be useful in detecting a dental artefact.

24. A dental tartar detection and removal system as defined in claim 23, wherein said monitor includes structure to show a representation of a broad range of wavelengths with boundaries representative of the predetermined range of values being indicated on said representation, said monitor structure also showing readings of said reflected light on said representation such that positions of said readings thereon relative to said boundaries are indicative of the presence or absence of said dental tartar.

25. A dental tartar detection and removal system as defined in claim 1, wherein said reflected light detector and analyzer comprises software for storing and/or updating data relative to the patient's history.

26. A dental tartar detection and removal system as defined in claim 1, wherein said tartar removal structure is integral with said probe.

27. A dental tartar detection and removal system of claim 1 wherein said reflected light detector and analyzer provides a signal to said operator when measurements on the reflected light at two or more wavelengths fall within a second predetermined range of values that are characteristic of artifacts other than tartar.

28. A dental tartar detection and removal system as defined in claim 1, wherein said probe distal end has a reduced cross-section suitable for insertion into a subgingival pocket to direct light and receive reflected light from tartar on a root of said tooth, and wherein said system is adapted for detection of tartar on said tooth within said subgingival pocket in the presence of blood.

29. A method for detecting and removing dental tartar, the method comprising:
using a probe to deliver incident light to a subgingival portion of a tooth surface, the incident light including at least one infrared wavelength that is transmitted through at least one of water and blood which is disposed on the surface of the tooth to reach and reflect from dental tartar which is disposed on the surface of the tooth in the subgingival portion thereof and beneath said at least one of water and blood;
receiving incident light that is reflected from said dental tartar which is disposed on the surface of the tooth in the subgingival portion thereof and beneath said at least one of water and blood;
using spectral reflectance detection to detect and analyze the at least one wavelength in the infrared range of the incident light that is reflected from said dental tartar which is disposed on the surface of the tooth in the subgingival portion thereof and beneath said at least one of water and blood to determine if said reflected light is representative of the presence of the dental tartar on the tooth surface;
providing a signal to an operator of said instrument when the presence of the dental tartar has been detected; and
responsive to said signal, actuating an ultrasonic tartar removal structure disposed in said probe to remove the detected tartar from the subgingival portion of the tooth surface.

30. A method as defined in claim 29, wherein the detecting and analyzing step comprises the step of comparing a value of said reflected light with a predetermined range of values that are characteristic of tartar.

31. A method as defined in claim 30, wherein said predetermined range of values covers wavelengths associated with spectral reflectance characteristics of tartar.

32. A method as defined in claim 31, wherein said predetermined range of values covers wavelengths associated with colours of tartar.

33. A method as defined in claim 29, wherein the step of using a probe to deliver incident light includes the steps of (i) delivering the incident light through at least one optical fibre having a distal end disposed adjacent the subgingival portion of the tooth, and (ii) providing said incident light from a light source to a proximal end of said at least one optical fibre such that the incident light emitted by said light source is transmitted by said optical fibre to the subgingival portion of the tooth, and
wherein the step of using spectral reflectance detection to detect and analyze the at least one wavelength includes the step of delivering the reflected light to an analyser using said at least one optical fibre.

34. A method as defined in claim 33, wherein the step of using a probe to deliver incident light and the step of using spectral reflectance detection to detect and analyze the at least one wavelength each use a different one of said at least one optical fibre.

35. A method as defined in claim 33, further comprising the step of using an irrigation system during said step of using a probe to deliver incident light, to deliver a fluid to a vicinity of the tooth.

36. A method as defined in claim 35, wherein said step of using an irrigation system includes the steps of (i) disposing a fluid supply tube distal end adjacent said distal end of each said at least optical fibre, and (ii) disposing a fluid source in fluid communication with said supply tube upstream of said tube distal end.

37. A method as defined in claim 36, wherein the step of using a probe to deliver incident light includes the step of disposing distal sections of (i) each said at least optical fibre and (ii) said supply tube, as a part of the probe.

38. A method as defined in claim 37, wherein said at least one optical fibre and said supply tube each comprises a proximal section that is detachably connected to said distal sections such that said distal sections and said probe are detachable from said proximal sections, and further comprising the step of discarding said distal sections and said probe and replacing them with new ones, or of sterilising said distal sections and said probe before being returned them to said proximal sections for further use thereof.

39. A method as defined in claim 29, wherein said step of providing a signal to the operator comprises the step of providing at least one of a light signal, a sound signal, and a vibration signal.

40. A method as defined in claim 29, wherein said step of providing a signal comprises the step of extracting the signal from a monitor including structure to show a representation of a broad range of wavelengths with boundaries representative of at least one predetermined range of wavelengths representative of the presence of tartar being indicated on said representation, said monitor structure also showing readings of said reflected light on said representation such that positions of said readings thereon relative to said boundaries are indicative of the presence or absence of tartar.

41. A method as defined in claim 29, wherein said step of using spectral reflectance detection comprises the step of comparing a value of said reflected light with a predetermined range of values that is characteristic of artefacts other than tartar that can be encountered by said probe along the tooth such that when said reflected light value does not fall within said predetermined range of values, said signal is sent to the operator.

42. A method as defined in claim 41, wherein said predetermined range of values cover wavelengths associated with spectral reflectance characteristics of said artefacts.

43. The method for detecting dental artefact as defined in claim 29, wherein said step of using a probe to deliver incident light includes the step of providing incident light having a 600 to 650 nm wavelength and providing incident light having a 800 to 920 nm wavelength.

44. A method as defined in claim 29, wherein said using a probe step comprises the steps of inserting a probe distal end into a subgingival pocket filled with blood, and displacing said probe distal end over a root surface of said tooth in said pocket.

45. A dental tartar detection and removal device, comprising:
   a probe having a distal end configured so as to be displaced along a subgingival portion of a tooth;
   a light source that delivers light to said probe distal end through one or more optic fibers, said light source delivering infrared light having a wavelength that (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof;
   a light intensity detector configured to collect the light reflected from said tartar and returned through said at least one of blood and water on the surface of the tooth in the subgingival portion thereof;
   an spectral reflectance analyzer configured to (i) utilize spectral reflectance detection to analyze the reflected light having said wavelength to detect the tartar in the subgingival portion of the tooth, and (ii) to provide a signal to an operator of said probe when said analysis detects said tartar, wherein said signal includes a detection signal carried by at least one of said one or more optic fibers to a location on the probe visible to said operator; and
   ultrasonic tartar removal structure integral with said probe and configured to remove the detected tartar.

46. The device as claimed in claim 45, wherein said light source delivers at least one light in the infrared range.

47. The device as claimed in claim 45, wherein said light source delivers light at two different wavelengths in ranges of (i) between about 600 to 650 nm and (ii) between about 800 to 920 nm, respectively.

48. A dental tartar detection and removal device comprising:
   a probe having a distal end configured to be displaced along a subgingival portion of a tooth;
   a light source that emits incident light at two or more spectrally distinct wavelengths wherein at least one of said wavelengths is in the infrared range, said two or more spectrally distinct wavelengths comprising at least one infrared wavelength which (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof;
   a first optical fiber configured to transmit the incident light to the probe distal end, and a second optical fiber configured to transmit light reflected from the tooth to a reflected light analyzer;
   said reflected light analyzer comprising a spectral reflectance light intensity detector configured to (i) utilize spectral reflectance detection to analyze the reflected light having said infrared wavelength to detect the tartar in the subgingival portion of the tooth, and (ii) to provide a signal to an operator of said probe when said analysis detects said tartar; and
   tartar removal structure coupled to said probe and configured to remove the detected tartar.

49. A device for detecting and removing dental tartar, comprising:
   a probe having a distal end configured to be displaced along a subgingival portion of a tooth;
   a light source that emits and provides incident light to said probe distal end, wherein said incident light comprises one or more wavelengths, one or more of which is in the infrared range and (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof;
   a light detector that (i) receives the returned light having the one or more infrared wavelengths reflected from said tooth at said probe distal end and (ii) detects said reflected light;
   a spectral reflectance light analyzer coupled to said light detector and configured to (i) utilize spectral reflectance detection to detect tartar on said tooth based on tartar reflectance properties and the returned light having the at said one or more infrared wavelengths, and (ii) to provide a signal to an operator of said probe when analysis on the returned light detects tartar; and
   tartar removal structure integral with said probe and configured to remove the detected tartar.

50. The device as defined in claim 49, wherein said incident light comprises two or more wavelengths, and wherein said spectral reflectance light analyzer detects tartar based on how a relative spectral composition of said two or more wavelengths is altered by reflection from the subgingival portion of the tooth.

51. The device as defined in claim 49, wherein said incident light further comprises light in the visible spectrum, and wherein said spectral reflectance light analyzer analyzes a ratio of (i) light detected at said one or more wavelengths in the infrared range and (ii) said light in the visible spectrum.

52. The device as defined in claim 51, wherein said light source comprises an LED emitting in the infrared range and an LED emitting in the visible range.

53. The device as defined in claim 49, wherein said light source comprises an LED emitting in the infrared range.

54. A method for detecting and removing dental tartar, the method comprising:

providing a probe having a distal end configured for displacing along a subgingival portion of a tooth while detecting and removing tartar, said probe having a tartar detection structure including a light source for projecting light onto a tooth root surface in the tooth subgingival portion and (ii) a light detector for detecting light returning from said tooth root surface, and said probe integrating a tartar removal structure, said light source projecting at least one infrared wavelength that (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof;

sliding the distal end of the probe in the tooth subgingival portion;

utilizing spectral reflectance detection to detect tartar in the tooth subgingival portion based on the returned at least one infrared wavelength;

generating an indication of the presence of tartar on the tooth subgingival portion during said sliding when said probe is in a position at which said tartar is detected, said generating providing an indication depending on analysis of said at least one infrared wavelength;

in response to said indication, removing tartar on the subgingival portion of the tooth without substantially moving said position; and repeating said sliding, said generating, and said removing until tartar is no longer detected on said root in said periodontal pocket.

55. A dental tartar detection and removal system, comprising:

a probe having a distal end adapted to be displaced along a tooth and within a subgingival pocket thereof;

a light source that delivers light through said probe distal end, said light including at least one wavelength in the infrared range that (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof;

a light detector that detects the returned light at said at least one wavelength that is reflected from said tooth, the reflected light being received at said probe distal end;

a spectral reflectance light intensity analyzer which uses spectral reflectance detection to provide a signal to an operator of said probe when measurements on the detected light, including said at least one wavelength in the infrared range, are characteristic of tartar reflectance; and a dental tartar removal apparatus incorporating said probe and operative to remove tartar on said tooth where said tartar is detected using said probe during displacement along the tooth subgingival portion.

56. A system as defined in claim 55, wherein said dental tartar removal apparatus comprises an ultrasound tartar removal device.

57. A system as defined in claim 56, further comprising an irrigation system integrated with said probe and which delivers fluid to the subgingival portion of the tooth when said probe distal end is in a periodontal pocket of said subgingival region.

58. A system as defined in claim 56, wherein said tartar removal apparatus is automatically activated by said signal.

59. A system for detecting and removing dental tartar, comprising:

a probe having a distal end configured so as to be displaced along a subgingival portion of a tooth;

a light source that emits incident light to said probe distal end, wherein said incident light comprises one or more wavelengths, one or more of which is in the infrared range that (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof;

a light detector that receives the returned light having the one or more wavelengths reflected from said tooth at said probe distal end and detects said reflected light;

a spectral reflectance light intensity detector coupled to said light detector and which (i) utilizes spectral reflectance detection to detect tartar on said tooth based on tartar reflectance properties and the reflected light at said one or more wavelengths in the infrared range, and (ii) provides a signal to an operator of said probe when analysis on the reflected light detects tartar; and a dental tartar removal apparatus configured to remove the detected tartar, wherein said dental tartar removal apparatus and said probe are configured to be held together by an operator such that, upon detection of the dental tartar, said removal apparatus can be actuated by the operator for removing at least some of the detected dental tartar.

60. A system for detecting and removing dental tartar, comprising:

a probe having a distal end configured to be displaced along a subgingival portion of a tooth;

a light source that provides incident light to said probe distal end, wherein said incident light comprises one or more wavelengths, at least one of which is in the infrared range that (i) transmits through at least one of blood and water on a surface of the tooth in the subgingival portion thereof, and (ii) reflects from tartar disposed beneath said at least one of blood and water on the surface of the tooth in the subgingival portion thereof, and (iii) returns through said at least one of blood and water on the surface of the tooth in the subgingival portion thereof;

a light detector that receives the returned light having the one or more wavelengths reflected from said tooth at said probe distal end and detects said reflected light;

a spectral reflectance light intensity analyzer coupled to said light detector and configured to (i) utilize spectral reflectance detection to detect tartar on said tooth based on tartar reflectance properties and the reflected light at said one or more wavelengths in the infrared range, and (ii) to provide a signal to an operator of said probe when analysis on the reflected light detects tartar; and a powered dental tartar removal apparatus, wherein said dental tartar removal apparatus is automatically controlled by said signal to remove the tartar.

* * * * *